United States Patent
Harroll et al.

(12)

(10) Patent No.: US 6,314,958 B1
(45) Date of Patent: Nov. 13, 2001

(54) FLUID CONTROL DRAPE WITH CONFORMING LIP

(75) Inventors: Bernadette A. Harroll, Baltimore, MD (US); Paul E. Lingeman, Carmel, IN (US)

(73) Assignee: Microtek Medical, Inc., Columbus, MS (US)

( * ) Notice: Subject to any disclaimer, the term of this patent is extended or adjusted under 35 U.S.C. 154(b) by 0 days.

(21) Appl. No.: 09/518,806

(22) Filed: Mar. 3, 2000

Related U.S. Application Data

(63) Continuation of application No. 08/868,704, filed on Jun. 4, 1997, now Pat. No. 6,070,586.
(60) Provisional application No. 60/019,206, filed on Jun. 5, 1996.

(51) Int. Cl.[7] .................................................. A61B 19/00
(52) U.S. Cl. ........................................... 128/849; 128/853
(58) Field of Search ...................................... 128/849–856

(56) References Cited

U.S. PATENT DOCUMENTS

| | | | |
|---|---|---|---|
| 3,540,441 | * | 11/1970 | Collins .................................. 128/855 |
| 4,598,458 | * | 7/1986 | McAllester ........................... 128/853 |
| 5,143,091 | * | 9/1992 | Patnode ................................. 128/853 |
| 5,161,544 | * | 11/1992 | Morris ................................... 128/849 |

OTHER PUBLICATIONS

Product brochure entitled "Innovation By Design . . . OB/Gyn Pouch Drapes," by Microtek Medical, Inc., Columbus, MS, 1994.
Product information sheet related to "Fluid Collection Under Buttocks Drape, 40"×44" " by Kimberly Clark.

* cited by examiner

*Primary Examiner*—Michael A. Brown
(74) *Attorney, Agent, or Firm*—Baker & Daniels

(57) ABSTRACT

A medical drape for controlling fluid during a medical procedure. The drape includes a base sheet formed of a fluid impervious material which is placed underneath a patient and on an operating bed. A sealing lip, which is made of a material such as a plastic encapsulated, compressible foam to conform to the underside of the patient, is attached to the base sheet in a fluid tight fashion and serves to achieve a fluid tight seal between the medical drape and the patient positioned thereon. The sealing lip rings a region of the base sheet and causes fluid that runs down along the patient above the base sheet to collect on the base sheet region, from where it is funneled to a fluid collection pouch. In an alternate embodiment, the medical drape is provided with a patient covering main sheet. A method of controlling fluid run-off during medical procedures with the a medical drape is also disclosed.

20 Claims, 12 Drawing Sheets

FLUID CONTROL DRAPE WITH CONFORMING LIP

CROSS-REFERENCE TO RELATED APPLICATION

This application is a continuation of U.S. application Ser. No. 08/868,704, filed Jun. 4, 1997, now U.S. Pat. No. 6,070,586.

This application claims the benefit under 35 U.S.C. § 119(e) of U.S. Provisional Application No. 60/019,206, filed Jun. 5, 1996.

BACKGROUND OF THE INVENTION

The present invention pertains to medical drapes, and, in particular, to a medical drape adapted to control fluid run-off during a medical procedure during which it is used.

Medical drapes are utilized in numerous types of surgical procedures and operations. Frequently, these drapes cover or overlay part or substantially all of the patients on whom procedures are being performed. These drapes have been designed to perform a variety of functions, including isolating the procedure site, and protecting the patient such as by reducing the likelihood for infection.

In many medical procedures, a patient lying on a hospital table or bed can be subject to contact with liquids. In a procedure such as an operative hysteroscopy, relatively large quantities of fluid are input into and output from a patient's uterus. The quantity of fluid input and output is closely watched as a loss of fluid can indicate a potential problem in the procedure. In an operative hysteroscopy, a surgical drape overlaying the patient can be provided with a pouch in which fluid running along the top surface of the drape can be collected such that the fluid is not lost and can be measured. However, on occasion, fluid can pass between the overlaying drape and the patient and run off onto the operating bed, and from there onto the floor of the operating room. This loss of fluid obviously adversely impacts the accuracy of the measurement of fluid output from the uterus. Besides potentially wetting operating room personnel, this fluid also can accumulate on the operating bed underneath the patient and remain there throughout the duration of the procedure, subjecting the patient to continuous contact with that fluid.

Fluid leakage is also a problem in medical procedures other than hysteroscopies. In some procedures, such as cystoscopies, the procedure may be performed using a specialized bed designed to collect the fluids that pass onto the patient. However, when performed in operating rooms lacking these specialized beds, cystoscopies are subject to the same fluid leakage problems as encountered during hysteroscopies.

Thus, it would be desirable to provide an apparatus for collecting fluid associated with medical procedures in a convenient yet relatively simple and inexpensive fashion.

SUMMARY OF THE INVENTION

The present invention provides a drape apparatus that can collect or redirect fluid running under a patient who is undergoing a medical procedure. The drape apparatus can be provided as a stand-alone drape or incorporated as a new feature into various styles of existing medical drapes. The drape apparatus includes a drip sheet with a conforming lip, preferably formed of plastic encapsulated foam, that adjusts to fit the contour of the underside of a patient positioned on the drape apparatus so as to form a fluid-tight seal with the patient to restrict the passage of fluid underneath the patient.

In one form thereof, the present invention provides a medical drape for controlling fluid during a medical procedure comprising a base sheet and a sealing lip. The base sheet, which is positionable between a patient and a patient supporting structure, comprises a fluid impervious material. The sealing lip is attached to the base sheet and at least partially circumscribes a surface of a region of the base sheet, which region surface comprises at least a part of the top or bottom surface of the base sheet The sealing lip comprises a construction adapted to conform to a contour of the patient to furnish a fluid-tight seal between the medical drape and patient; whereby the top surface of the base sheet region serves as a collection area for fluid that during the medical procedure may drain along a part of the patient above the base sheet region.

In another form thereof, the present invention provides an underbuttocks drape for controlling fluid reaching a buttocks area of a patient on an operating table during a medical procedure, comprising a base sheet and a sealing lip. The base sheet, which is positionable on the operating table underneath the patient, comprises a fluid impervious material and a top surface. The sealing lip is attached to the base sheet top surface in a fluid tight manner and at least substantially circumscribes the top surface of at least a portion of the base sheet operationally positioned under the patient's buttocks area. The sealing lip includes a compressible foam construction adapted to conform to a contour of the patient around the buttocks area of the patient as the patient rests on the medical drape positioned on the operating table. The sealing lip is adapted to fill gaps between the base sheet and the patient such that the sealing lip causes fluid running along the buttocks area of the patient to drain along the top surface of the at least a portion of the base sheet.

In still another form thereof, the present invention provides a method for controlling fluid during a medical procedure on a patient comprising the steps of providing a patient support platform comprising an upper surface and an edge, positioning the patient on the patient support platform, and providing a fluid control drape. The fluid control drape comprises a base sheet formed of a fluid impervious material, and means, adapted to conform to a contour of the patient resting thereon, for providing a fluid-tight seal with the patient to route fluid to a collection area of the top surface of the base sheet at least partially surrounded by the fluid-tight seal means. The method further comprises the step of positioning the base sheet on the patient support platform upper surface such that a buttocks area of the patient positioned on the patient support platform is disposed above the base sheet and the fluid-tight seal means sealingly engages the patient, whereby fluid that runs down along the buttocks area of the patient above the base sheet collection area operatively encounters the fluid-tight seal means and is routed to the collection area of the base sheet top surface.

One advantage of the present invention is that it provides an underbuttocks drape that effectively controls fluids that may pass under a patient during certain surgical procedures.

Another advantage of the present invention is that it provides for an underbuttocks drape that allows fluids that pass under a patient during surgery to be collected so as to be measured.

Another advantage of the present invention is that its design makes it easy to install and use properly.

Still another advantage of the present invention is that fluid run-off underneath a patient is controlled without any absorption of the fluid that may interfere with keeping accurate track of fluid quantities.

BRIEF DESCRIPTION OF THE DRAWINGS

The above mentioned and other advantages and objects of this invention, and the manner of attaining them, will become more apparent and the invention itself will be better understood by reference to the following description of embodiments of the invention taken in conjunction with the accompanying drawings, wherein.

Figure 1:
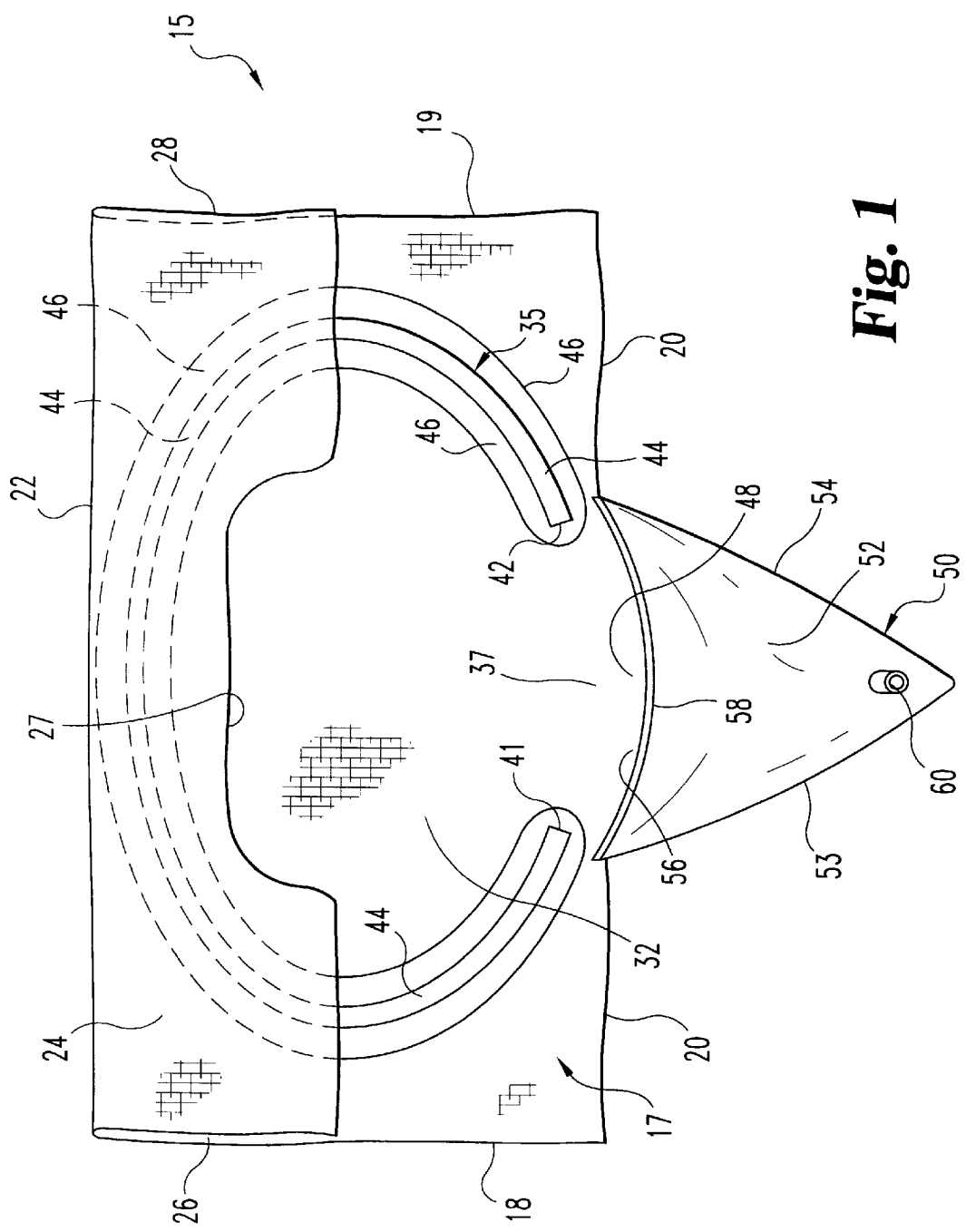
FIG. 1 is a top view of a first embodiment of a fluid control drape of the present invention in a generally flat arrangement.

Corresponding reference characters indicate corresponding parts throughout the several views. Although the drawings represent multiple embodiments of the present invention, the drawings are not necessarily to scale and certain features may be exaggerated or omitted in some of the drawings in order to better illustrate and explain the present invention.

DESCRIPTION OF THE PREFERRED EMBODIMENTS

Referring now to FIG. 1, there is shown a top view of a first embodiment of a fluid control drape with a patient conforming lip of the present invention. The drape, generally designated 15, is shown in a generally flat arrangement to which it can be unfolded from its shipped or stored arrangement. When operationally positioned over a support structure such as an operating bed or table as further described below, drape 15 will generally assume the arrangement shown in FIGS. 2—4.

Figure 2:
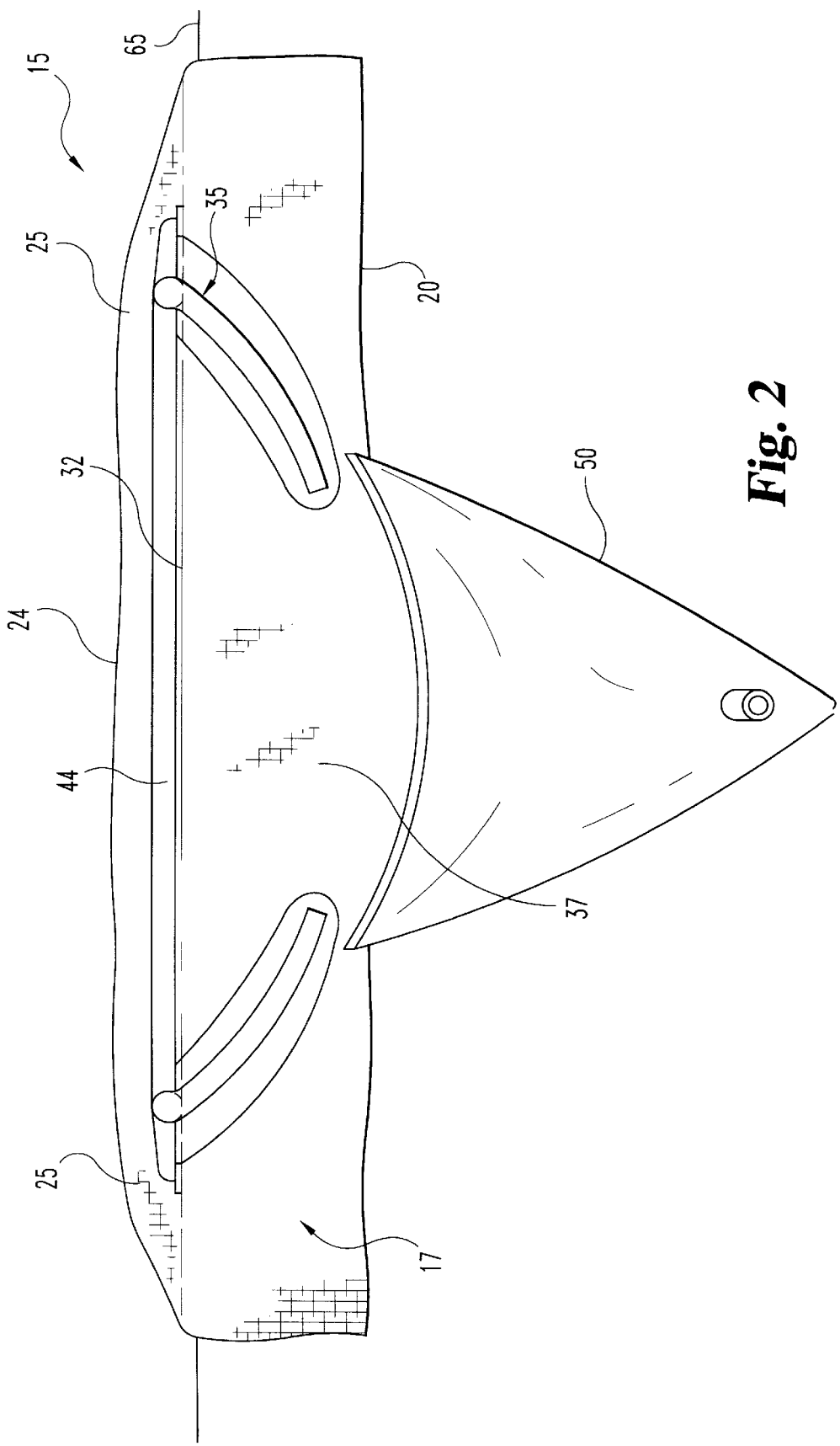
FIG. 2 is a front view of the drape of FIG. 1 after it has been placed on an operating table/bed so as to partially hang over the bed, wherein the top surface of the bed is shown diagrammatically as a horizontal line.
Figure 4:
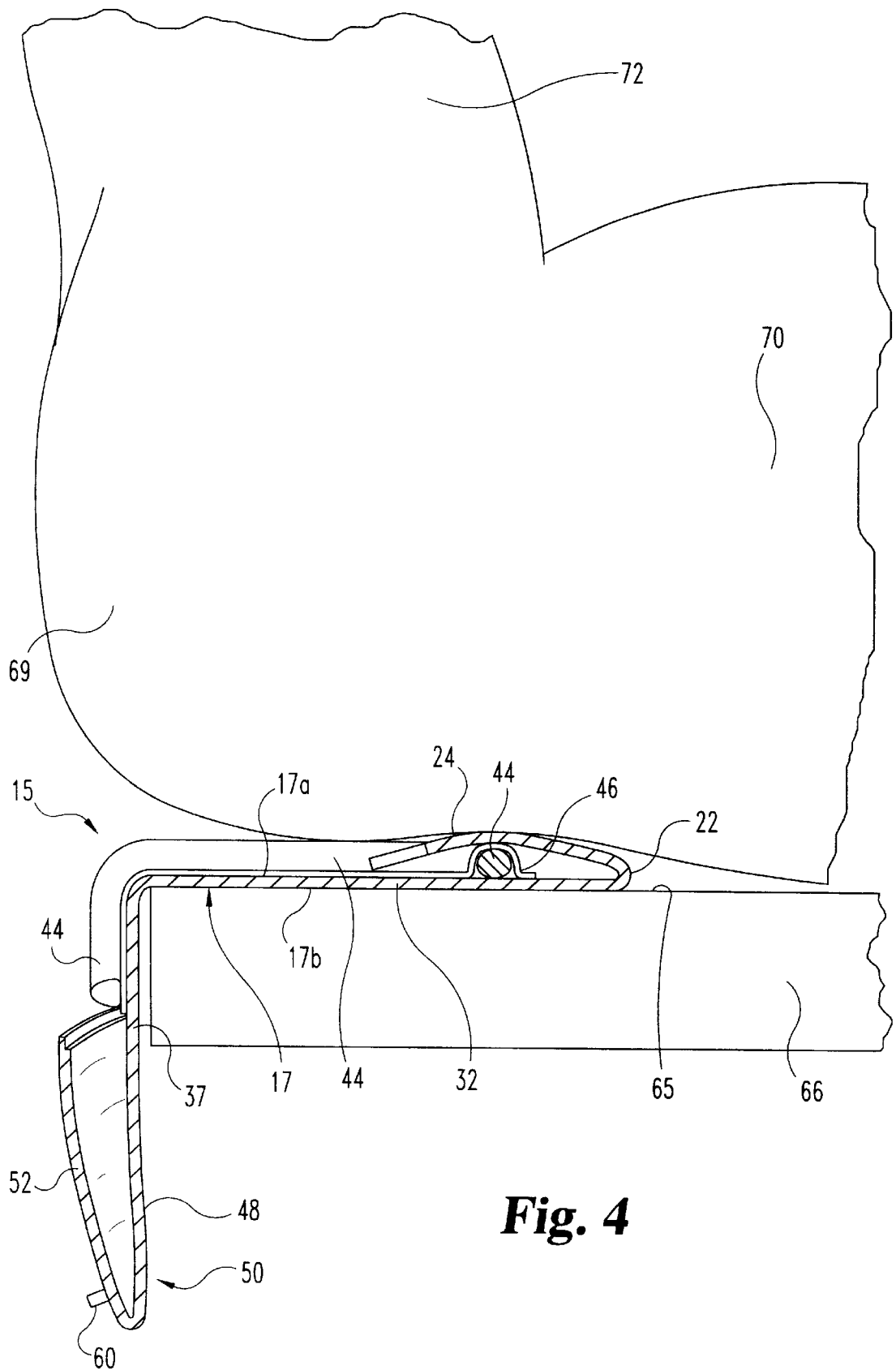
FIG. 4 is a cross-sectional side view of the fluid control drape taken along line 4—4 in FIG. 3, wherein the patient, on whom a procedure is to be performed, is abstractly shown lying on the drape with her buttocks area in sealing contact with the conforming lip of the drape.

Drape 15 includes a base or drip sheet 17, which is generally shown as having a rectangular outline. As best shown in FIG. 4, base sheet 17 includes a top surface 17a and a bottom surface 17b. With directions in reference to FIG. 1, base sheet 17 includes opposite side edges 18, 19, a bottom edge 20 and a top edge portion 22. Along the entire length of edge portion 22, flap or section 24 of base sheet 17 is folded down over the top portion of base sheet 17 to provide a cuff that extends the entire side-to-side width of base sheet 17. A cut-out area or notch 27 formed in the bottom edge of cuff 24 provides an opening by which more of the top surface of drip sheet 17 is exposed to allow fluids to drip directly thereon. Along the entire length of the side edges of the cuff, the folded over flap 24 of base sheet 17 is secured or attached as indicated at 26 and 28, such as by heat sealing, to the part of base sheet 17 overlaid. As shown in FIG. 2, cuff 24 forms a single pocket 25 between the upper surface of base sheet 17 and the underside of cuff 24 that accommodates the hands of operating room personnel as described below.

Figure 3:
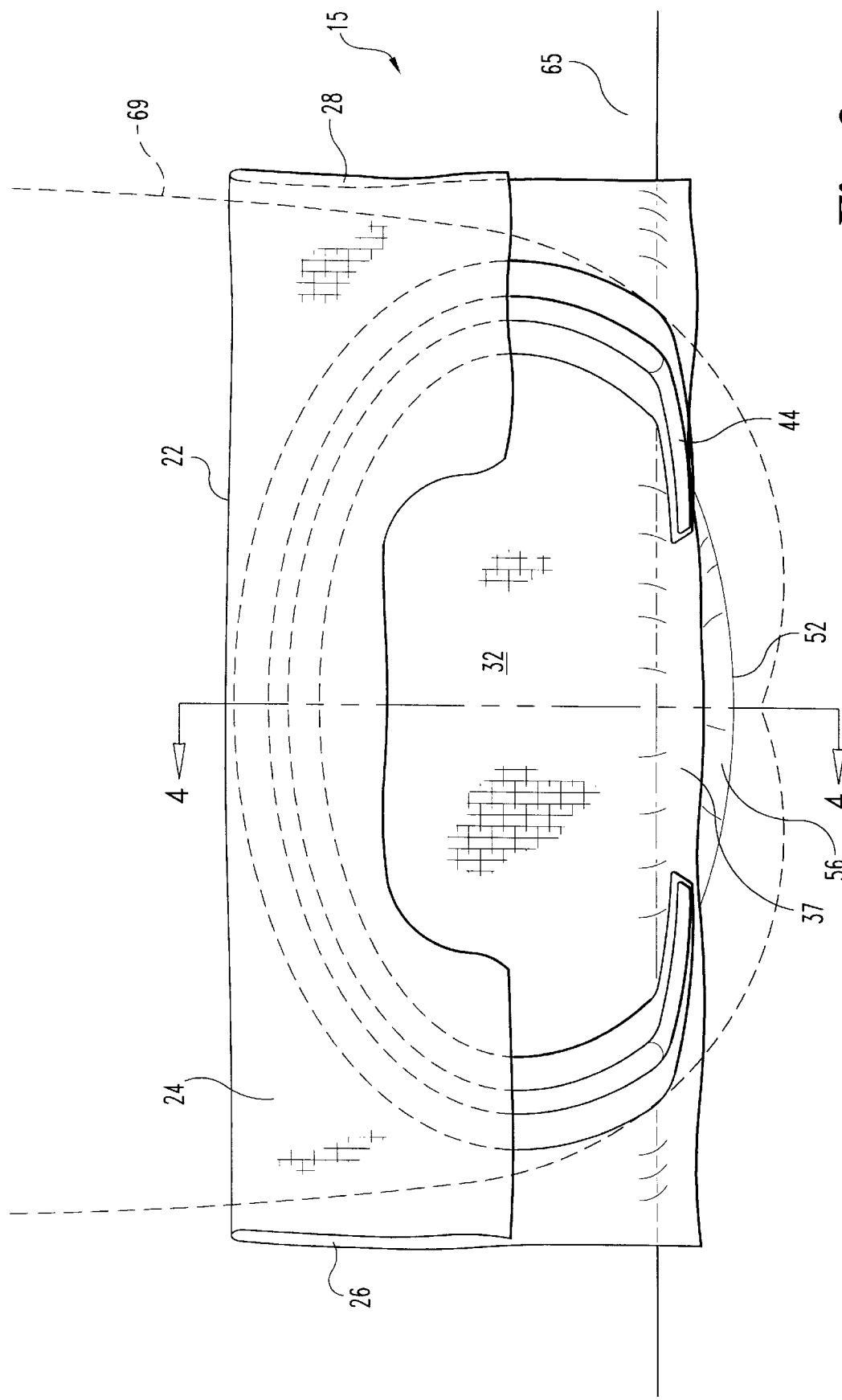
FIG. 3 is a top view of the fluid control drape and bed of FIG. 2, wherein the outline of a patient positioned on the drape is generally shown in dashed lines.
Figure 10:
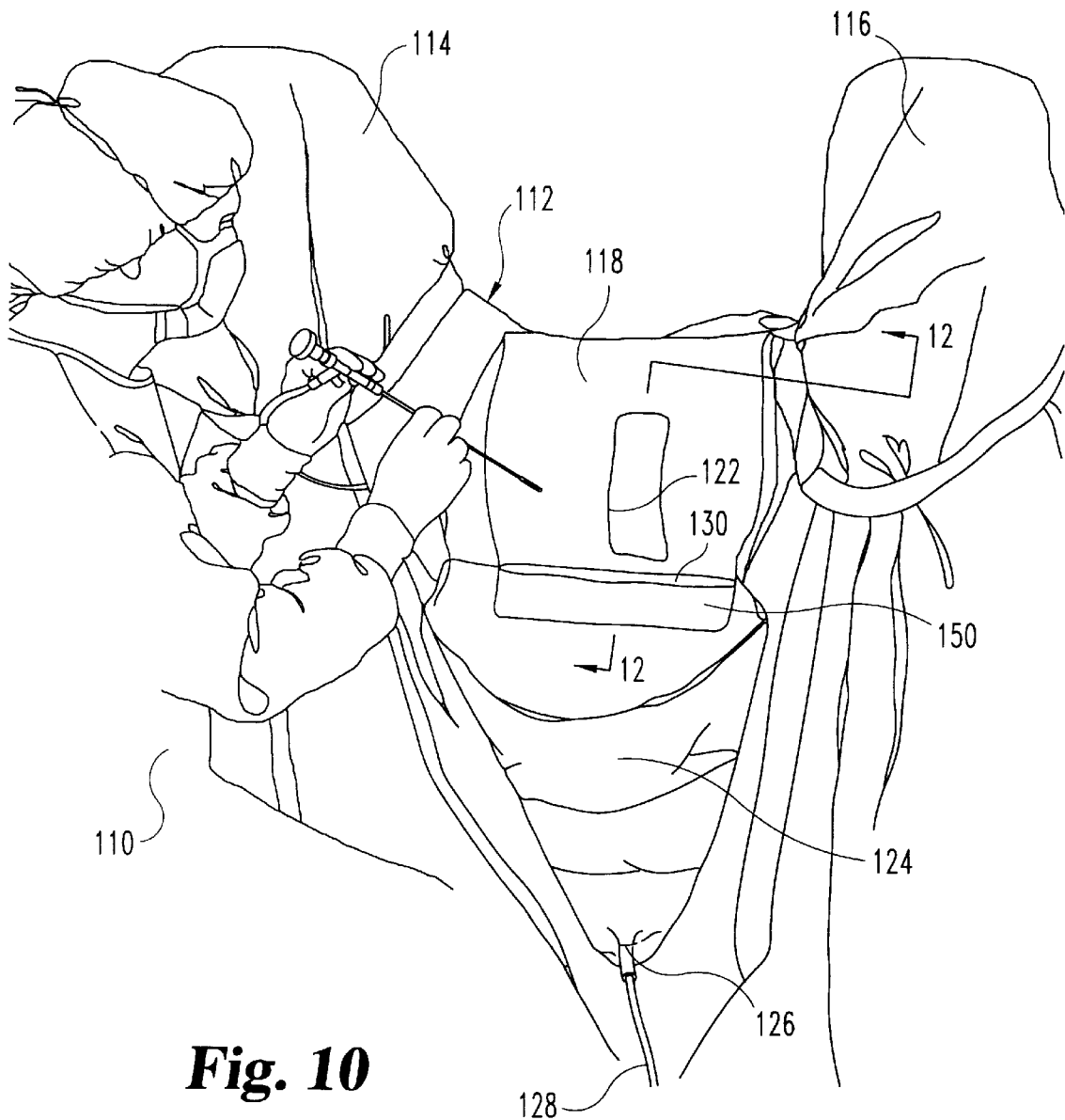
FIG. 10 is a front view of a medical drape of the present invention being used to cover a patient during a medical procedure.

Drip sheet 17 has a centrally located, generally elliptical base region 32 which is partially ringed or circumscribed by a sealing lip 35 described further below and which in the embodiment of FIGS. 1–4 is partially covered by cuff 24. An unringed portion 37 of base sheet region 32 that extends between ends 41 and 42 of sealing lip 35 serves as an outlet conduit along which fluids are conveyed that reach and collect on base region 32. Drip sheet 17 is formed of a thin layer of a flexible, and to at least a limited extent tear-resistant, material so as to be arrangeable as shown in FIGS. 2–4 and to insert and fit comfortably under a patient. The drip sheet material is fluid impervious to prevent fluids that reach drip sheet 17 from passing therethrough. One suitable material for drip sheet 17 is a tear-resistant, flexible sheet of plastic, such as a six mil thick, clear, low density/ethylene vinyl acetate polyethylene film. Alternatively, a disposable, non-woven material or fabric which also finds useful application in the making of other medical drapes, such as shown in FIG. 10, that overlay patients may be employed. This type of non-woven material is commercially available, for example, as Product No. 9315 from Dexter Corporation, Non-Wovens Division of Windsor Locks, Connecticut.

Circumscribing base sheet region 32 almost entirely is sealing rim or lip 35 that is adapted to conform to a patient lying, reclining or otherwise positioned on drape 15. The term circumscribe is intended herein to refer to the act of extending around a surface area of the base sheet, and is not limited to circular or elliptical shapes. In order for lip 35 to tightly seal the space between drip sheet 17 and a patient with whom drape 15 is advantageously employed, lip 35 is constructed to conform to the contour of the patient. One preferred manner of furnishing a conforming lip 35 is to form lip 35 out of a compressible, solid foam material, for example a material in a lightweight cellular form resulting from the introduction of gas bubbles during manufacture, such as foamed plastic. One suitable, solid foam material is a polyurethane foam having a density of about 2.5 pounds per cubic foot and an indented load deflection rating of about 14, but other foams may be employed within the scope of the invention. Alternate conforming constructions, such as an inflatable or air-filled lip, may also be employed within the scope of the invention.

Lip 35 is generally shown in the Figures as having a solid foam core 44 with a uniform, generally circular cross-section. The cross-sectional shape and size of core 44 may be varied, provided a suitable fluid seal is achieved between drape 15 and the patient during use. For example, in a preferred embodiment, core 44 has a flat base to set flush on base sheet 17, and further includes a flattened top surface with undulations along its ellipse-forming length. Core 44 is wrapped by a layer of a fluid impervious material 46 to prevent fluid absorption within core 44. As shown in FIG. 4, layer 46 extends over the sides and top of foam core 44, and the layer edges are completely heat sealed in a fluid-tight fashion to the top surface of base sheet 17. Wrapping layer 46 is formed from a three mil thick sheet of the same material as base sheet 17.

In an alternate embodiment, instead of providing a patient conforming sealing lip, a fluid retaining rim having a rigid construction which is not compressible or conforming but which projects from the top surface of the base sheet may be substituted for the sealing lip on the medical drape. This fluid retaining rim will contain fluid accumulating on the top surface of the base sheet such that the fluid does not run under the patient but instead is funneled toward a fluid collection pouch of the drape.

As shown in FIG. 4, a triangular extension 48 of drip sheet 17 forms the back wall of a flexible, fluid collection pouch 50. The front wall 52 of pouch 50 is formed of the same material as wrapping layer 46 and is heat sealed along the length of edges 53 and 54 to provide a leakage-free pouch. The upper edge of front wall 52 is longer than the length of extension 48 along bottom edge 20 such that the front wall 52 bows outward to form an opened pouch mouth portion 56 through which passes fluid flowing through run-off conduit 37. A moldable wire 58 within a plastic cover heat sealed to front wall 52 ensures mouth portion 56 remains open during use. Pouch 50 is abstractly shown including an openable and closeable outlet valve 60. Rather than this shown construction where the pouch is partially integrally formed with base sheet 17, pouch 50 may alternatively be separately formed and secured with adhesives or other suitable fasteners to drip sheet 17. It will be appreciated that any fluid which runs down the top surface of drip sheet 17 along conduit 37 passes into pouch 50 during operation. The pouch alternatively may be formed as a more sturdy, rigid pouch shaped element if desired, or may be provided as the end of a larger conduit connected to a fluid receptacle.

Referring now to FIGS. 2–4, drape 15 is shown in its operational arrangement. FIG. 2 is a front view of drape 15 mounted on the end of an operating bed, with the top surface of the bed indicated at 65. FIG. 3 is a top view of FIG. 2, with the outline of the buttocks and lower torso of a patient lying on drape 15 being generally shown in dashed lines at 67. FIG. 4 is a cross-sectional side view of FIG. 3 where drape 15 is underneath the buttocks 69 of a patient. The lower portion of a patient's torso is represented at 70, and the thigh region of a patient's leg is shown at 72. The remainder of the patient's leg, which may be mounted in stirrups for selected procedures, is not shown in FIG. 4.

Drape 15 will typically be an accessory used in conjunction with other types of medical drapes that overlay much if not all of the patient. Such other drapes, which may be any of a variety of drape styles well known in the art, are not shown in FIGS. 2–4 for clarity of illustration. Drape 15 also may be used by itself without any other medical drapes. If necessary, drape 15 may be provided as a sterilized unit, and such sterilization may be performed in any suitable manner known in the art.

In preparing for the procedure requiring its usage, drape 15 is placed on bed 66 (See FIG. 4). Specifically, drip sheet base region 32 is positioned on the generally horizontal top surface 65 of the end of bed 66, and the drip sheet conduit portion 37 and pouch 50 are allowed to hang over the edge of bed 66. Typically, drape 15 is inserted underneath a patient already reclining on bed 66. This insertion is effected by a person in the operating room placing his/her hands into pocket 25 at the opposite, upper corners of the cuff 24 and thrusting the drape 15, with edge portion 22 leading, under the patient. In an alternate embodiment, cuff 24 may be replaced with loops placed along the top edge of base sheet 17 which may be gripped to allow the drape to be pulled under a patient. At this point, drape 15 is generally arranged as shown in FIGS. 2–4. The drape alternatively may be positioned on the table before the patient, and in such cases the drape will normally be non-sterile.

When drape 15 is inserted, the buttocks 69 of the patient rests on drape 15. The patient's buttocks may actually contact the top surface of base sheet region 32. The positioning of the patient over drape 15 can be adjusted by, for example, moving the drape along the bed more forward or more rearward than the position shown in FIG. 4. As shown, the solid foam construction allows lip 35 to compressibly conform or adjust to fit the contour of the patient's buttocks area. The length of drape 15 is preferably such that for most patients the rearward (toward the patient's head) extent of sealing lip 35 reaches a point near the upper end of the patient's buttocks, and preferably between the small of the patient's back and the coccyx. The exact position of the sealing lip relative to tile patient may depend on the positioning of the patient along the length of the table, which positioning may be adjusted based on the preferences of the medical staff. One drape size suitable for many adult patients extends thirty inches between edges 18 and 19, fifteen inches between top edge portion 22 and edge 20, and with base sheet region 32 forming an approximately twenty-three inch by fourteen inch ellipse with the gap between lip ends 41 and 42 measuring about ten inches. Differently sized and shaped base sheets and sealing lips may be employed depending on the positioning, as well as size, of the patient to provide suitable fluid collection capabilities.

During a medical procedure such as a hysteroscopy on the patient, irrigating fluid or the like may pass below a surgical drape (not shown) covering the patient and run down along the central region of the patient's buttocks. This fluid then passes into or drips down onto drip sheet base region 32. Lip 35 prevents fluid from running along the patient's buttocks either laterally or rearwardly beyond the region covered by drip sheet base region 32. As the fluid drips onto drip sheet region 32 and collects thereat, it flows under gravity down conduit portion 37 and into pouch 50. Outlet valve 60 can be connected to one end of a piece of tubing (not shown), and the other end of the tubing in turn can be connected to a suction port, a larger collection receptacle, or even back to the bottom of a larger collection pouch possibly provided on the patient-covering surgical drape. Rather than directly connecting to the pouch on the patient-covering drape, tubing from outlet valve 60 could be connected to a Y-shaped connector that also connects in flow communication with both a tubing from the collection pouch of the patient-covering drape and a drain tubing through which fluid inlet to the Y-shaped connector from both of the other tubings drains. After the medical procedure is completed, drape 15 may be disposed of as appropriate.

The inventive drape apparatus may be alternately configured and arranged from the embodiment shown in FIG. 1 within the scope of the invention. Referring now to FIGS. 5–8, drape 85 includes a central, flexible drip sheet 87, which is generally shown as having an outline similar to that of a light bulb. Drip sheet 87 has a generally circular base portion 89 which tapers to a neck portion 91 that serves as an outlet conduit along which fluids are carried away that collect on base portion 89. Drip sheet 87 is fluid impervious to prevent fluids that reach drip sheet 87 from passing therethrough.

Ringing the perimeter of drip sheet 87 is a rim or lip 93 adapted to conform to a patient positioned on drape 85. Along its underside, lip 93 is secured in a fluid-tight manner to the top surface of drip sheet 87, such as with a durable adhesive or glue or via a heat seal.

In order for lip 93 to tightly seal the space between drip sheet 87 and a patient with whom drape 85 is advantageously employed, lip 93 is formed as an inflatable tube that will conform to a patient's underside. The inflatable tube forming lip 93 can be inflated and deflated through the use of a valve, diagrammatically shown at 95, which allows fluids to be selectively inlet and outlet. Air or possibly other gaseous or liquid mediums may be employed. The type of valve used can be one of an assortment of well known designs. For example, the valve could be of the type which is automatically opened and closed upon the insertion of a syringe type device, which can be used to introduce air into lip 93.

Lip 93 is generally shown in the Figures as having a circular cross-section, and is further shown tapering in diameter from the segment ringing base portion 89 to the segments aligned along the sides of drip sheet neck portion 91. The cross-sectional shape and size may be varied, provided a suitable fluid seal is achieved with the patient during use.

Lip 93 may be formed from one or more different types of materials. One suitable material is a stretchable plastic that outwardly expands like a balloon during inflation. Alternatively, lip 93 may be formed out of a flexible, generally fluid or air impervious material which can be inflated or deflated, but which does not exhibit marked stretching upon inflation, but rather upon inflation simply fills a given volume. Although described as being inflatable/deflatable, lip 93 could be permanently inflated or filled.

Figure 5:
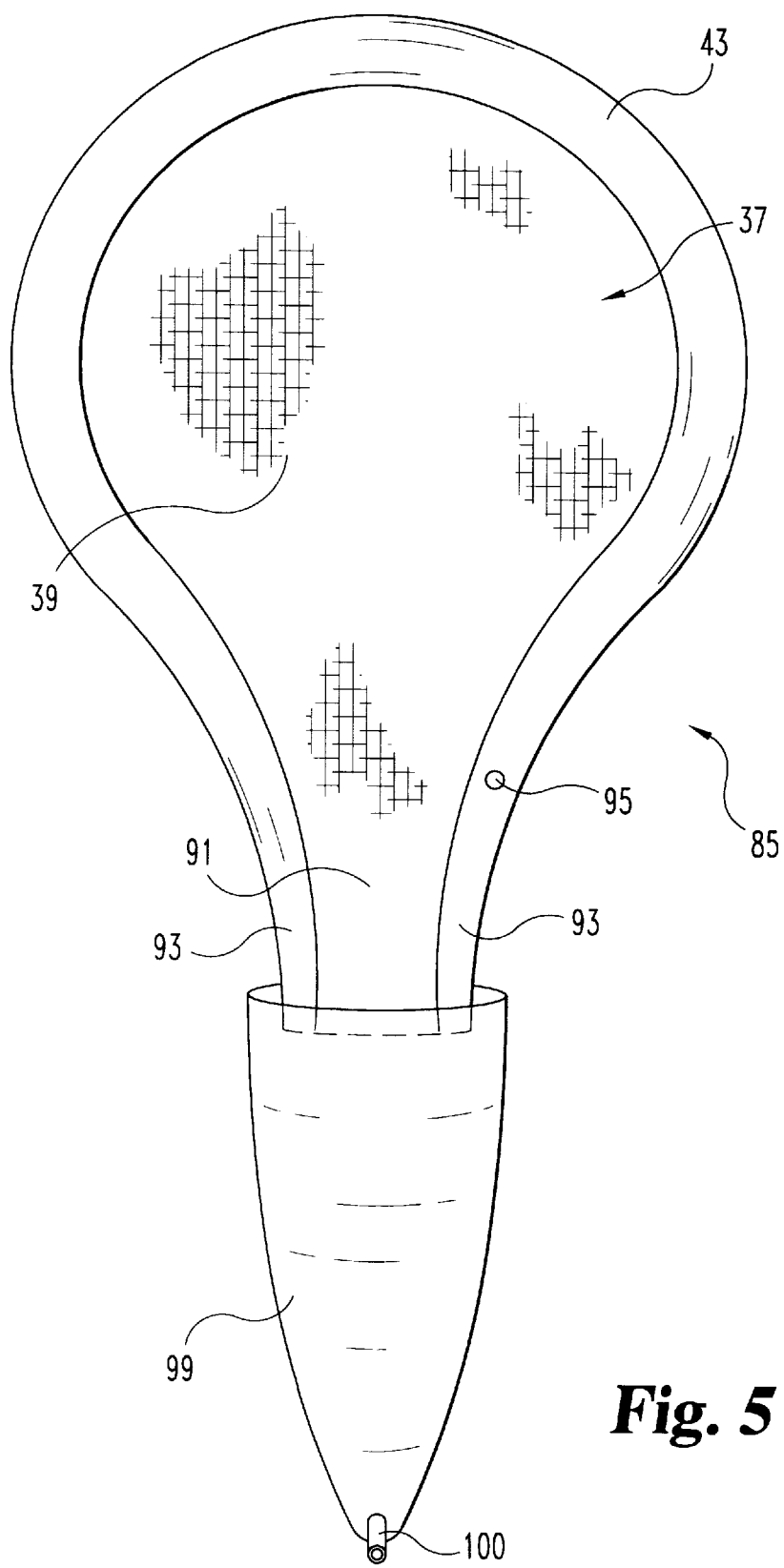
FIGS. 5–8 are views, conceptually similar to the views of FIGS. 1–4, respectively, of a second embodiment of a fluid control drape of the present invention.

The lower ends of drip sheet 87 and lip 93, which are shown in dashed lines in FIG. 5, insert within the top of a flexible, collection pouch 99. Pouch 99 may be formed of any suitable plastic or fluid impervious material, and is shown including an openable and closeable outlet valve 100. Drip sheet 87 is secured with adhesives or other suitable fasteners at the upper edge of collection pouch 99. Drip sheet 87 is secured on the inside surface of pouch 99 such that any fluid which runs down the top surface of drip sheet 87 passes into pouch 99 during operation.

Although lip 93 is shown as containing a single internal compartment, filled through a single valve 95, which rings the entire perimeter of drip sheet 87, other lip configurations are possible. For example, lip 93 may be segmented into multiple compartments with separate valves associated with particular compartments, and with such a design different air pressures can be provided along different segments of the lip. In addition, with separate compartments, different compartments may be filled or pre-filled with different mediums. In an alternate embodiment, the lip segment ringing base portion 89 and under the patient may be air filled while the lip segments flanking neck portion 91 and hanging over the bed edge may be foam filled, or vice versa.

Figure 6:
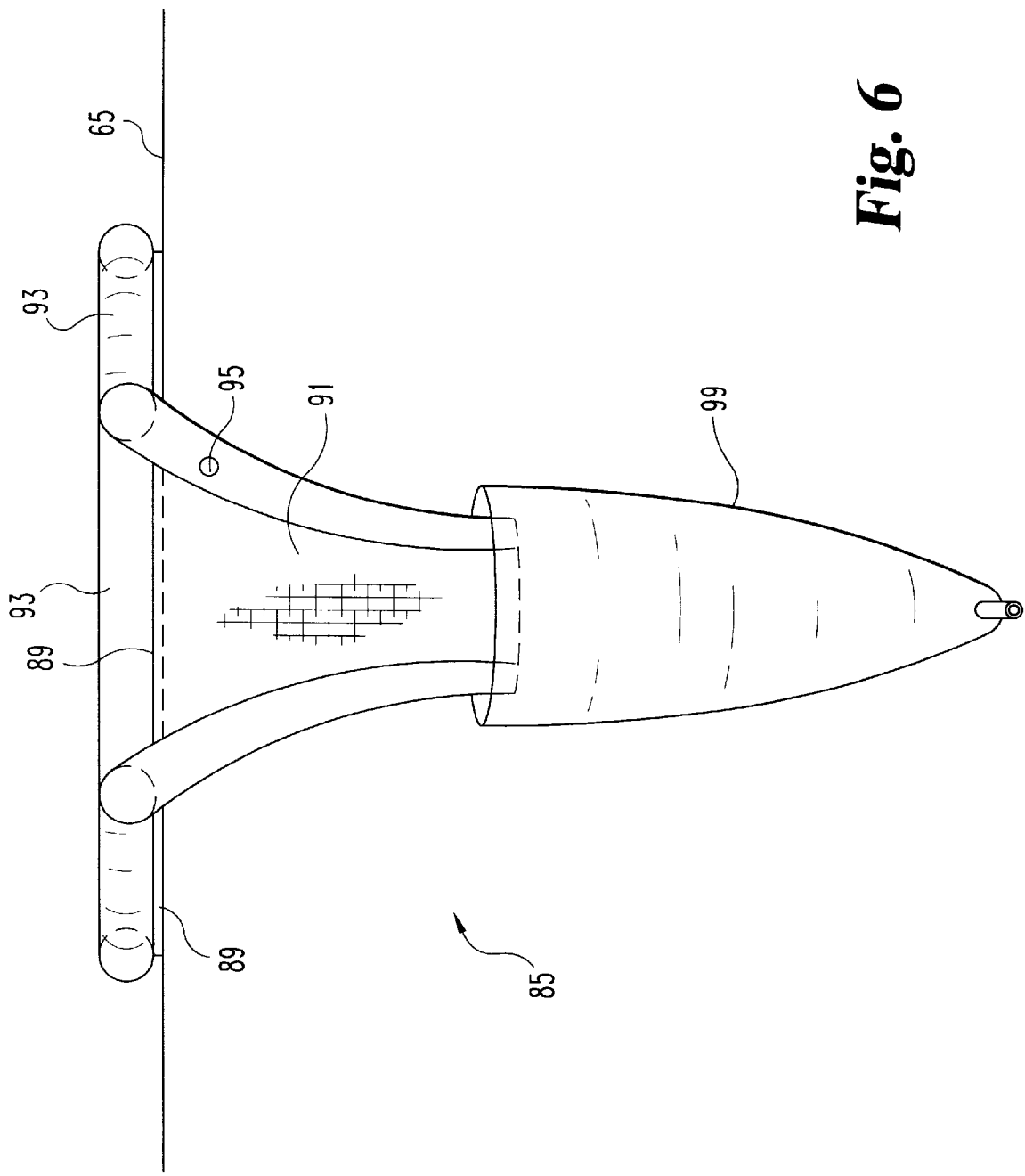
Figure 7:
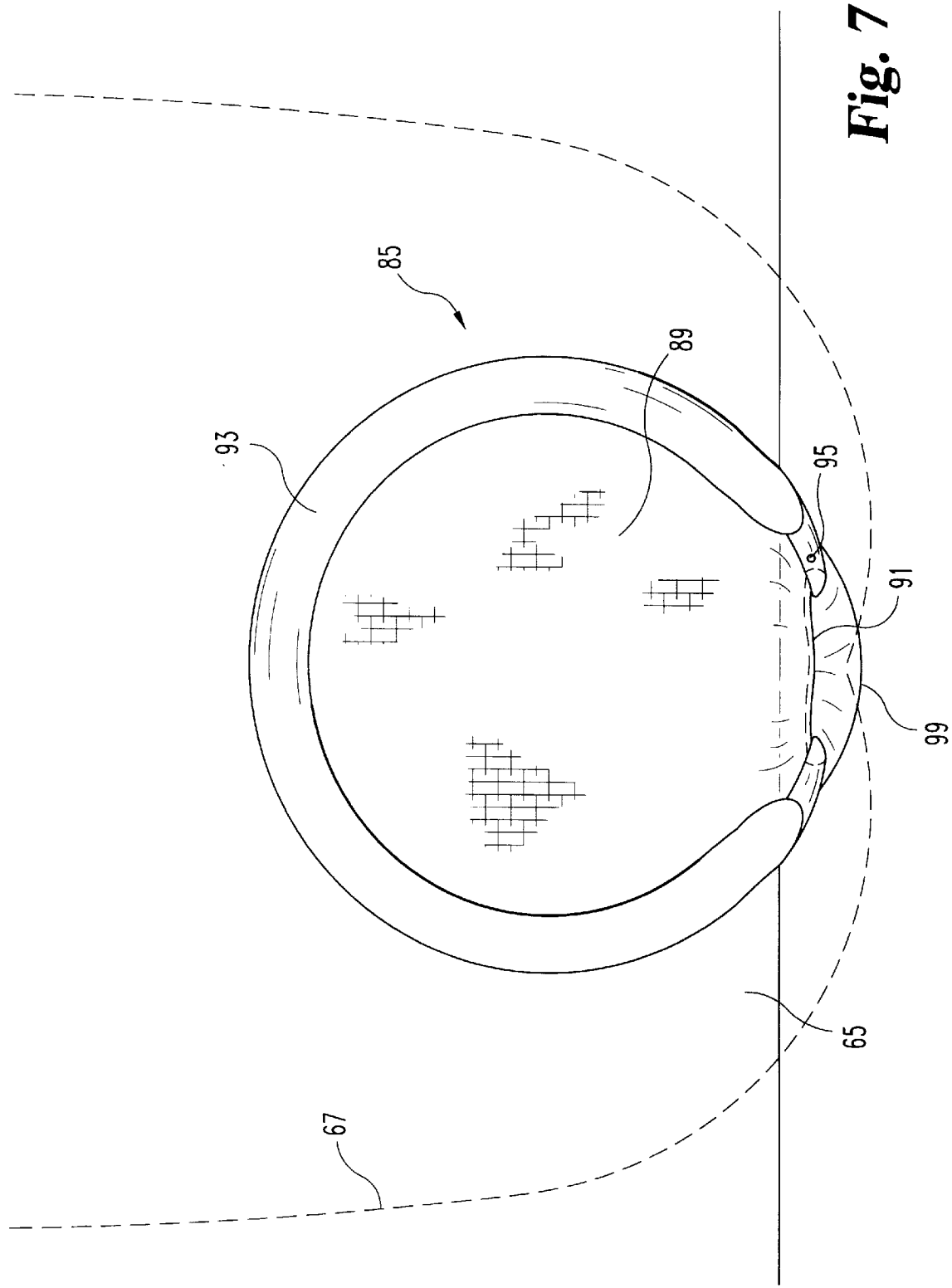
Figure 8:
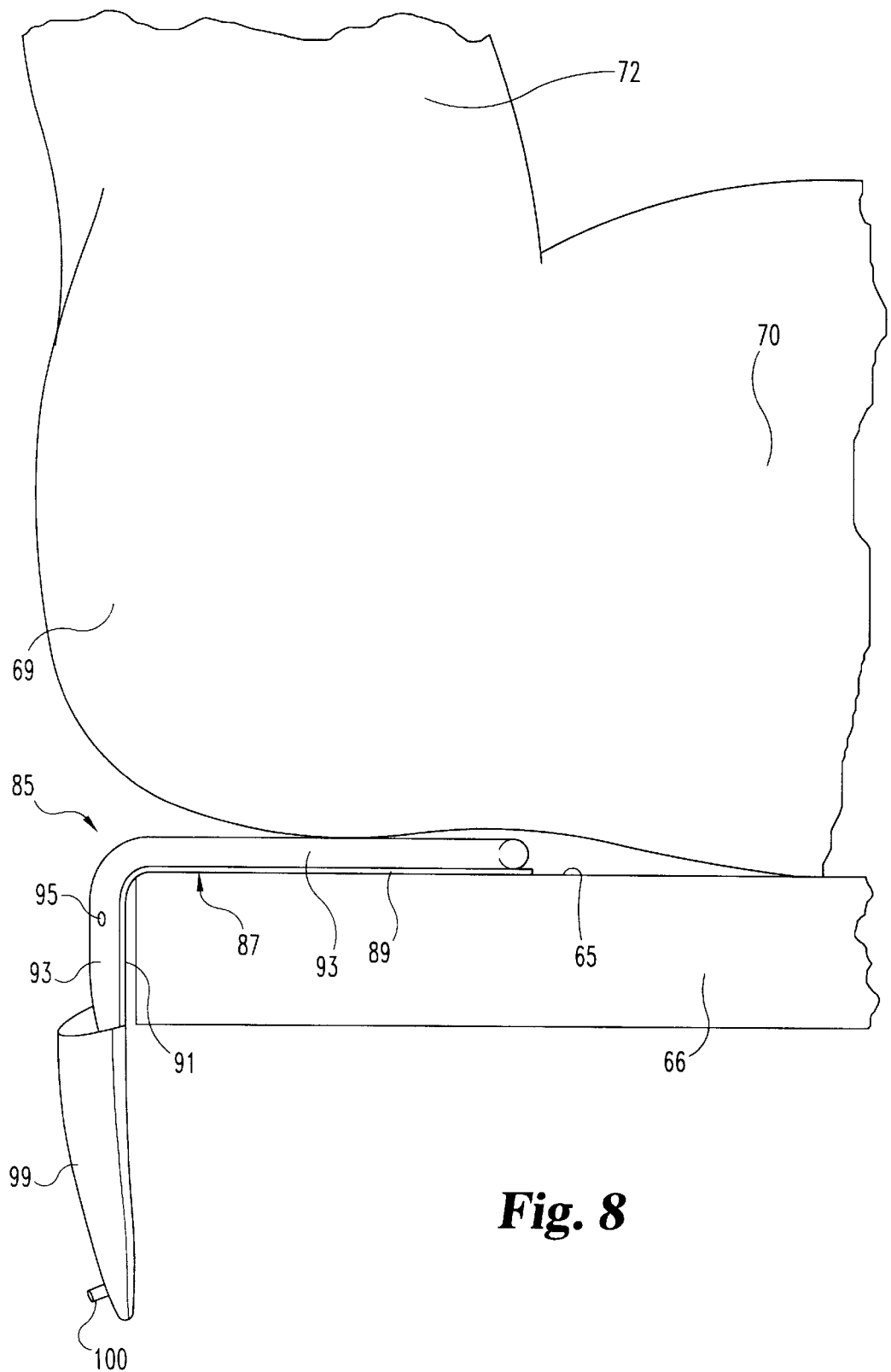

Referring now to FIGS. 6–8, drape 85 is shown in its operational arrangement. Parts of the patient and operating table similar to the parts described with reference to the embodiment of FIGS. 1–4 are similarly numbered. In preparing for the procedure requiring its usage, drip sheet base portion 89 is positioned on the generally horizontal top surface 65 of the end of bed 66, and the drip sheet neck portion 91 and pouch 99 are allowed to hang over the edge of bed 66. Either before or after a patient is moved onto drape 85, drape lip 93 is inflated. If drape 85 is provided sterile, the lip should be inflated after the drape is placed under the patient, and a cuff should be provided to prevent contamination during insertion. The inflation of the lip segments flanking neck portion 91 may cause neck portion 91 to bow upward from the generally vertical orientation shown, but this does not interfere with the flow of fluid. At this point, drape 85 is generally arranged as shown in FIGS. 6 and 7. The patient is then positioned on bed 66 with her buttocks 69 resting on drape 85 as shown in FIG. 8.

During a medical procedure, fluid that runs down along the central region of the patient's buttocks passes into or drips down onto drip sheet base portion 89. Lip 93 prevents fluid from running along the patient's buttocks either laterally or rearwardly beyond the region covered by drip sheet 87. As the fluid drips onto drip sheet 87 and collects thereat, it flows under gravity down neck portion 91, into pouch 99, and then through outlet valve 100 into an attached tube. The inflated lip segments lining the edges of neck portion 91 aid in preventing fluid from missing pouch 99.

Figure 9:
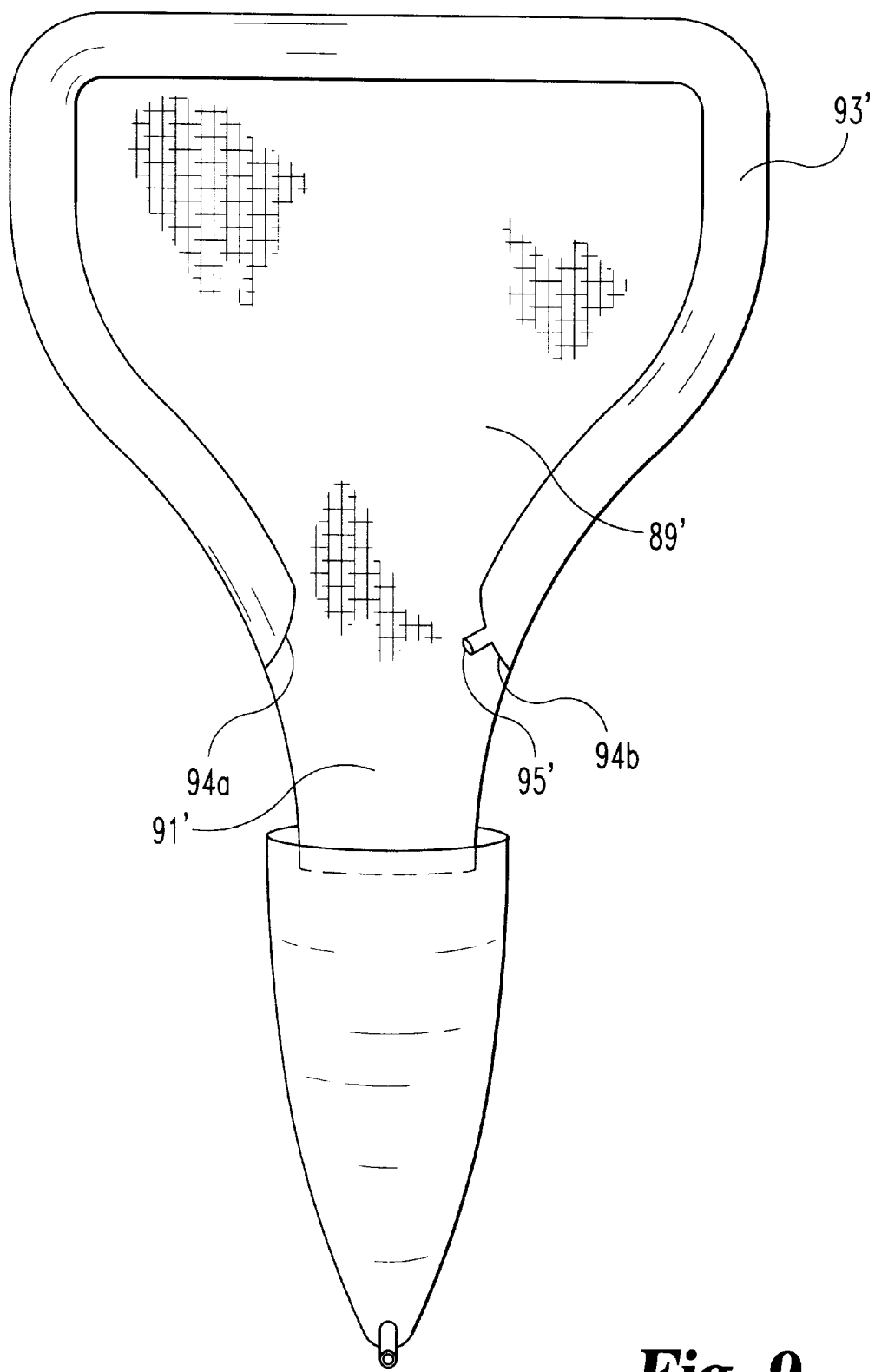
FIG. 9 is a top view of a third embodiment of a fluid control drape of the present invention.

In FIG. 9, another embodiment of the present invention is shown in which the drip sheet base portion 89' has a generally flat edge. Moreover, in this embodiment, lip 93' terminates at ends 94a and 94b and does not reach the pouch. The inflation valve in this embodiment is shown at 95'. The drip sheet neck portion 91' could be provided with rims to better ensure fluid collected on base portion 89' reaches the shown pouch. Such rims need not be inflatable or conforming because with proper drape placement they would never come in contact with the patient during usage.

Referring now to FIG. 10, there is shown another embodiment of the present invention being used in the performance of a urologic or gynecologic endoscopy procedure. In this embodiment, a fluid collecting drape apparatus similar to that disclosed in FIGS. 1–4 has been incorporated and integrated into a medical drape used to cover the entire patient.

Referring to FIG. 10, a patient, lying on her back, is undergoing a gynecologic procedure performed by physician 110. The patient is covered by a medical drape 112 which includes leg covering portion 114, 116 that overlay the patient's legs mounted in stirrups. A central portion 118 of drape 112 is provided with a rectangular shaped, operative opening or fenestration indicated at 122. The patient facing surface of drape central portion 118 completely ringing fenestration 122 is provided with an adhesive which is secured directly to the patient. A pre-attached bag or pouch 124 used to collect fluids is adhesively connected to drape 118. Bag 124 includes a drainage port 126 connected with tubing 128. Drapes of the above-described type are available as a 3 in 1 Procedure Drape from Lingeman Medical Products of Indianapolis, Indiana.

Below fenestration 118 is a second opening through the drape which is indicated at 130. Opening 130 is shown being a generally horizontally aligned rectangle in shape. Other opening shapes and orientations alternatively could be employed. For example, an upwardly opening arcuate opening or circular opening could be used, and such designs might further aid in ensuring fluid passes through the opening and out from under drape 112 as described further below. Although shown as passing through drape 112 between fenestration 122 and the upper edge of pouch 124, opening 130 may be formed to open directly into the interior volume of pouch 124, or be spaced from the pouch such that fluid passing through opening 130 runs along the top surface of the drape into the pouch.

Figure 11:
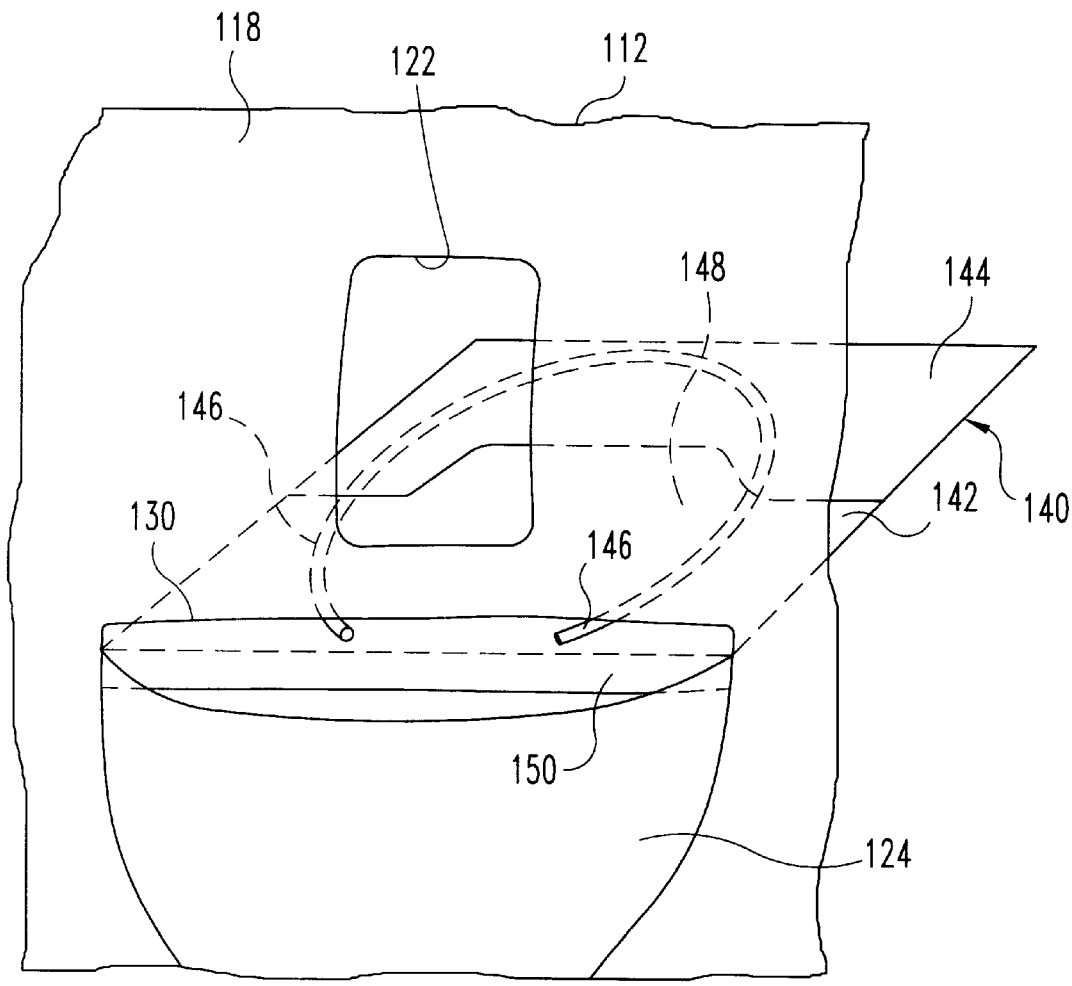
FIG. 11 is a partial perspective view of the drape of FIG. 10, wherein the fluid control portion insertable beneath a patient is further shown.

Referring now to FIG. 11, there is shown a cut away perspective view of a portion of the drape 112 shown in FIG. 10. Specifically, shown is central drape portion 118 including fenestration 122, the upper portion of pouch 124 and the fluid collecting drape portion which is inserted underneath the patient and which is generally designated 140. Drape portion 140 is provided sterile as with the remainder of drape 112. With the exception of the manner in which its fluid collection pouch is provided, fluid collecting drape portion 140 is formed identical to drape 15 of FIGS. 1–4.

Drape portion 140 generally includes a base sheet 142, cuff 144, a sealing lip 146 constructed of a plastic encapsulated foam core, and an elliptical drip region 148. The bottom or proximate edge portion 150 of base sheet 142 extends through opening 130 and overlays and is attached, preferably by heat seal but alternatively by other fasteners including adhesives, to the back panel of pouch 124. This drape construction results in fluid running off of drip region 148, through the gap between the ends of sealing lip 146, and along the edge portion 150 through opening 130 and down into pouch 124.

Figure 12:
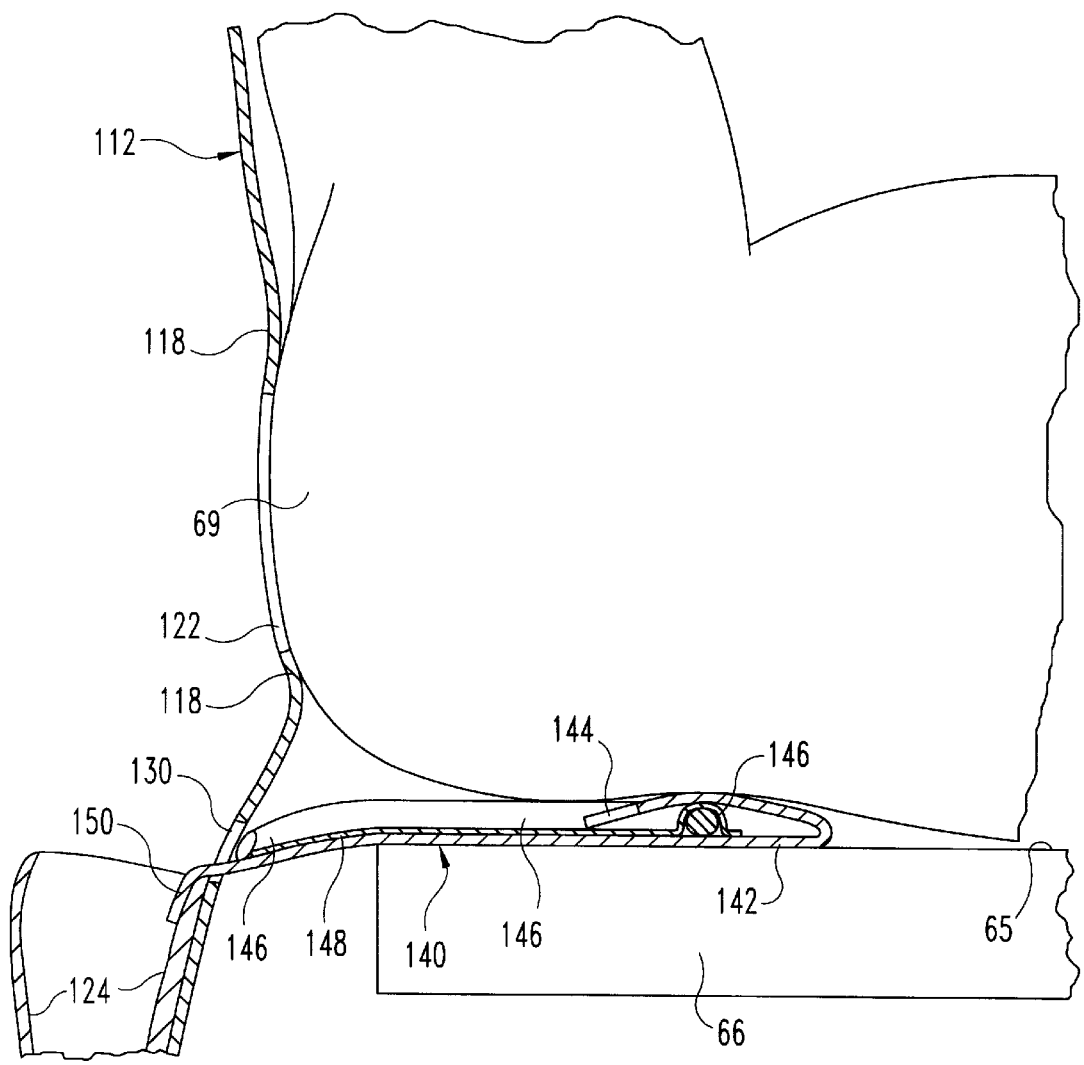
FIG. 12 is a side cross-sectional view, taken along line 12—12 in FIG. 10, of the drape of the present invention, wherein the patient with whom the drape is being utilized is shown abstractly.

As shown in FIG. 12, which is a cross sectional side view as taken along line 12—12 of FIG. 10, opening 130 is preferably provided at a height along medical drape 112, relative to fenestration 122, which results in the bottom edge of opening 130 being slightly below the level of top surface 65 of bed 66 to facilitate fluid flow. During use, typically the adhesive rectangle adhering drape central portion 118 to the patient prevents fluid from escaping underneath the patient. On occasion, however, a proper seal between the patient and drape is not achieved, and fluid passes between drape 112 and the patient. The fluid runs along the patient's buttocks 69 and drips onto collection region 148. The seal achieved with buttocks 69 directly by lip 146, and additionally or alternatively directly by cuff 144, prevents the fluid from passing toward the patient's head beyond collection region 148. The collected fluid then passes under gravity along base sheet 142 and out through opening 130 as described above.

A separate opening 130 is not required within the scope of the invention. In an alternate embodiment, edge portion 150 may be connected to the bottom edge of fenestration 122 so that fluid collected in collection region 148 pours out onto the top surface of drape 112 through fenestration 122. Such a design works best if fenestration 122 extends down farther than is shown in FIG. 12 so fluid does not overflow the sealing lip 146. In another not shown alternate embodiment, the sealing lip may completely encircle in a fluid-tight fashion the collection region 148 so as to define a basin on base sheet 142 in which fluid could be held after collection. The fluid held within the basin could be drained therefrom in an alternate fashion, such as with a downwardly extending tube opening at its top end into the basin and connectable at its bottom end to pouch 124 of drape 112 or to an auxiliary pouch.

To use the invention, fluid collecting drape portion 140 is placed on the operating bed and underneath the reclining patient as part of the draping procedure and prior to the adhesive rectangle around fenestration 122 being attached to the patient. After the drape portion 140 is finally positioned underneath the patient, the adhesive rectangle is secured. After the procedure is completed, drape portion 140 is disposed of with the rest of drape 112.

While this invention has been shown and described as having preferred designs, the present invention may be modified within the spirit and scope of this disclosure. For example, the sealing lip could be placed on the underside of the drape and the foam lip would aid in keeping the base sheet in fluid-tight contact with the patient. This application is therefore intended to cover any variations, uses, or adaptations of the invention using its general principles. Further, this application is intended to cover such departures from the present disclosure as come within known or customary practice in the art to which this invention pertains.

What is claimed is:

1. A medical drape for controlling fluid during a medical procedure comprising:

a base sheet positionable between a patient and a patient supporting structure, said base sheet including a fluid impervious material and a top surface and a bottom surface;

a sealing lip attached to said top surface of said base sheet and at least partially circumscribing the top surface of a region of said base sheet, wherein all of said base sheet region having a top surface at least partially circumscribed by said sealing lip is continuous, wherein said continuous region surface includes at least a portion of said base sheet top surface and said base sheet bottom surface, said sealing lip including a construction adapted to conform to a contour of the patient to furnish a fluid-tight seal between the medical drape and patient; and whereby said top surface of said base sheet continuous region serves as a collection area for fluid that during the medical procedure may drain along a part of the patient above said base sheet continuous region.

2. The medical drape of claim 1 wherein said sealing lip is attached in a fluid-tight manner to said base sheet top surface.

3. The medical drape of claim 2 further comprising a fluid collection pouch connected to one of said base sheet and said sealing lip, wherein said sealing lip comprises a discontinuity formed between first and second ends of said sealing lip such that said sealing lip fails to form a continuous fluid barrier around said base sheet region, wherein said fluid collection pouch comprises a mouth portion opening into an internal volume of said pouch, said mouth portion being structured and arranged to admit fluid draining off of said top surface of said base sheet region between said sealing lip first and second ends.

4. The medical drape of claim 2 wherein said sealing lip is arranged to directly contact and seal against a patient during use.

5. The medical drape of claim 2 further comprising means for facilitating the insertion of said base sheet and said sealing lip underneath the patient positioned on the patient supporting structure.

6. The medical drape of claim 5 wherein said means for facilitating insertion comprises a cuff folded over said base sheet to form at least one hand-receiving pocket between said cuff and said base sheet.

7. The medical drape of claim 6 wherein said cuff overlays at least a portion of said sealing lip, and wherein an edge of said cuff overlaying said sealing lip comprises a notched section over said base sheet region.

8. The medical drape of claim 1 wherein said sealing lip comprises a compressible foam.

9. The medical drape of claim 8 wherein said foam comprises a core of said sealing lip, wherein said sealing lip comprises a fluid impervious wrapping of said core, and wherein said wrapping is attached in a fluid tight manner to said base sheet top surface.

10. The medical drape of claim 1 further comprising a main sheet sized and shaped to overlay the patient during the medical procedure, said main sheet comprising a fenestration through which the patient overlaid with said main sheet is accessible, said base sheet attached to said main sheet.

11. The medical drape of claim 10 wherein said main sheet comprises an aperture proximate the attachment of said base sheet and said main sheet, wherein said sealing lip comprises a discontinuity formed between first and second ends of said sealing lip whereby said sealing lip fails to form a continuous fluid barrier around said base sheet region, wherein said main sheet aperture is structured and arranged to permit fluid draining off of said top surface of said base sheet region and between said sealing lip first and second ends to pass through said main sheet.

12. The medical drape of claim 11 further comprising a pouch attached to said main sheet for collecting fluid passing along an upper surface of said main sheet, and wherein said pouch is adapted to also collect fluid passing through said main sheet aperture.

13. An underbuttocks drape for controlling fluid reaching a buttocks area of a patient on an operating table during a medical procedure, comprising:

a base sheet positionable on the operating table underneath the patient, said base sheet comprising a fluid impervious material and a top surface;

a sealing lip attached to said base sheet top surface in a fluid tight manner, said sealing lip, except for a single discontinuity, continuously circumscribing said top surface of at least a portion of said base sheet operationally positioned under the patient's buttocks area, said sealing lip comprising a compressible foam construction adapted to conform to a contour of the patient around the buttocks area of the patient as the patient rests on the underbuttocks drape positioned on the operating table, said sealing lip adapted to fill gaps between said base sheet and the patient such that said sealing lip causes fluid running along the buttocks area of the patient to drain along said top surface of said at least a portion of said base sheet; and a fluid handling system comprising a mouth portion connected to said base sheet, wherein said single discontinuity of said sealing lip furnishes a fluid run-off conduit along said base sheet, and wherein said fluid handling system is structured and arranged to admit into said mouth portion any fluid draining off of said top surface of said at least a portion of said base sheet and along said fluid run-off conduit.

14. The underbuttocks drape of claim 13 wherein said sealing lip further comprises a wrapping of a fluid impervious material around a core constructed of said compressible foam, whereby said sealing lip is non-absorbent.

15. The underbuttocks drape of claim 13 further comprising a cuff means attached to said base sheet for facilitating operationally positioning said base sheet and said sealing lip underneath the patient on the operating table.

16. The underbuttocks drape of claim 15 wherein said cuff means overlays at least a portion of said sealing lip and is sandwiched by the patient against said sealing lip.

17. An underbuttocks drape for controlling fluid reaching a buttocks area of a patient on an operating table during a medical procedure, comprising:

a base sheet positionable on the operating table underneath the patient, said base sheet comprising a fluid impervious material and a top surface;

a fluid retaining rim upwardly protruding from said base sheet top surface, said fluid retaining rim comprising a first end, a second end, and a length extending continuously from said first end to said second end, said length of said fluid retaining rim at least substantially circumscribing said top surface of at least a portion of said base sheet operationally positioned under the patient's buttocks area;

wherein all of said portion of said base sheet having a top surface at least substantially circumscribed by said fluid retaining rim length is continuous;

whereby said top surface of said base sheet portion operationally positioned under the patient's buttocks area serves as a collection area for fluid that during the medical procedure may drain along the patient's buttocks area; and wherein a space between said first and second ends of said fluid retaining rim permits fluid to drain along said top surface off of said portion of said base sheet having a top surface at least substantially circumscribed by said fluid retaining rim length.

18. The underbuttocks drape of claim 17 further comprising a fluid collection pouch connected to said base sheet, said fluid collection pouch comprising a mouth portion opening into an internal volume of said pouch, said mouth portion being structured and arranged to admit fluid draining along said top surface through said space between said first and second ends of said fluid retaining rim.

19. A medical drape for controlling fluid reaching a buttocks area of a patient on an operating table during a medical procedure, comprising:

a base sheet positionable on the operating table underneath the patient, said base sheet including a fluid impervious material and a top surface;

a sealing lip attached to said base sheet top surface in a fluid tight manner, said sealing lip at least partially circumscribing the top surface of a region of said base sheet, wherein all of said base sheet region having a top surface at least partially circumscribed by said sealing lip is continuous, said sealing lip comprising a construction adapted to conform to a contour of the patient to furnish a fluid-tight seal between the base sheet top surface and patient;

whereby said top surface of said base sheet continuous region serves as a collection area for fluid that during the medical procedure may drain along a part of the patient above said base sheet continuous region;

a main sheet sized and shaped to overlay the patient during the medical procedure, said main sheet including a fenestration through which the patient overlaid with said main sheet is accessible, said base sheet attached to said main sheet, said main sheet including an aperture distinct from said fenestration and proximate the attachment of said base sheet and said main sheet, wherein said sealing lip includes a discontinuity formed between first and second ends of said sealing lip whereby said sealing lip fails to form a continuous fluid barrier around said base sheet continuous region, wherein said main sheet aperture is structured and arranged to permit fluid draining off of said top surface of said base sheet continuous region and between said sealing lip first and second ends to pass through said main sheet.

20. The medical drape of claim 19 further comprising a pouch attached to said main sheet for collecting fluid passing along an upper surface of said main sheet proximate said fenestration, and wherein said pouch is adapted to also collect fluid passing through said main sheet aperture.

* * * * *